(12) United States Patent
Ho (10) Patent No.: US 11,918,528 B2
(45) Date of Patent: Mar. 5, 2024

(54) DEVICES AND METHODS FOR CLEANING EXCREMENT

(71) Applicant: Chin-Hsuan Ho, New Taipei (TW)

(72) Inventor: Chin-Hsuan Ho, New Taipei (TW)

(73) Assignee: Chin-Hsuan Ho, New Taipei (TW)

( * ) Notice: Subject to any disclaimer, the term of this patent is extended or adjusted under 35 U.S.C. 154(b) by 0 days.

(21) Appl. No.: 17/872,019

(22) Filed: Jul. 25, 2022

(65) Prior Publication Data

US 2023/0030078 A1    Feb. 2, 2023

(30) Foreign Application Priority Data

Jul. 30, 2021  (TW) .................................. 110128195
Feb. 10, 2022  (TW) .................................. 111104983

(51) Int. Cl.
*A61G 9/02*    (2006.01)
*A61G 9/00*    (2006.01)

(52) U.S. Cl.
CPC ............... *A61G 9/02* (2013.01); *A61G 9/003* (2013.01)

(58) Field of Classification Search
CPC ............ A61G 9/02; A61G 9/003; A61F 5/451
USPC ....... 4/300.2, 300, 450, 300.3, 301, 415, 302
See application file for complete search history.

(56) References Cited

U.S. PATENT DOCUMENTS

2022/0186482 A1*    6/2022 Lin .......................... E03D 1/003

* cited by examiner

*Primary Examiner* — Lori L Baker (57) ABSTRACT

An excrement cleaning device comprises a body made of hard material and a cup body made of soft material. The body comprises a base, a support base, a flushing member, and a cleaning member. The support base is longitudinally formed at a rear end of the base. At least one water outlet is provided at the top of the support base. The flushing member is extendingly disposed at the base and is connected to the flushing port. The cleaning member is embedded in the support base. One side of the cup body is disposed at the body while the other side comprises a cup opening. A periphery of the cup opening is provided with a lip in contact with hip of user. A sheet body of the lip extends outward to form a hip enclosing area corresponding to the hip.

8 Claims, 7 Drawing Sheets

DEVICES AND METHODS FOR CLEANING EXCREMENT

CROSS-REFERENCE TO RELATED APPLICATION

This application claims the priority benefit of Taiwanese Patent Application Serial Number 110128195, filed on Jul. 30, 2021, and Taiwanese Patent Application Serial Number 111104983, filed on Feb. 10, 2022, the full disclosure of which is incorporated herein by reference.

BACKGROUND

Technical Field

The present disclosure relates to the technical field of cleaning device, in particular to a cleaning device and an associated cleaning method for those who cannot take care of their excrement.

Related Art

Patients who were bedridden for a long time and could not get out of bed to take care of their excrement, in the past, needed caregivers or family members to assist in cleaning up. The common practice was to use diapers. Diapers are normally changed as soon as being contaminated, then clean diapers are put on after patients are washed and wiped. However, most patients at first would resist diapering, with the feeling of uncomfortable and disrespect.

To deal with the problems above, a device has been developed that can automatically clean up after detecting excrement, without the assistance of others. A common disadvantage of such a device is that it requires a specific bed. Holes need to be made in the mattress to allow the lines/wires/tubes to pass through the mattress to connect with the cleaning device and to ensure that excrement can be detected and cleaned. Chinese Patent No. 105358112A discloses an automatic excrement disposal device that does not require holes in the mattress. However, such a device still has many problems, which is mainly the complicated and bulky structural configuration, inconvenient for cleaning.

Thus, it is necessary to develop a device with a simpler structure, which could accurately detect and drive the device for cleaning on conventional beds, in addition to the need for special mattresses.

SUMMARY

The embodiments of the present disclosure provide an excrement cleaning device in a modular structural design tended to simplify the overall assembly process to facilitate cleaning and relevant maintenance.

In one embodiment, the present disclosure provides an excrement cleaning device connected to a processing device, comprising a body made of hard material and a cup body made of soft material. The body comprises a base, a support base, a flushing member, and a cleaning member. The base is provided with a flushing port, a suction inlet, a hot air port, and a cleaning port. The flushing port is connected to the processing device through a flushing water tube. The suction inlet is connected to the processing device through an excrement tube. The hot air port is connected to the processing device through a hot air tube. The cleaning port is connected to the processing device through a cleaning water tube. The support base is longitudinally formed at a rear end of the base. At least one water outlet is provided at the top of the support base. The flushing member is extendingly disposed at the base and is connected to the flushing port. The cleaning member is embedded in the support base. One end of the cleaning member is connected to the cleaning port while the other end is connected to the water outlet. One side of the cup body is disposed at the body while the other side comprises a cup opening. A periphery of the cup opening is provided with a lip in contact with hip of user. A sheet body of the lip extends outward to form a hip enclosing area corresponding to the hip.

Thus, compared with the complicated structural configuration of conventional excrement cleaning devices, the present disclosure applies a simple two-pieces modular structural design, which could set the cup body made of soft material with the sheet body on the body made of hard material to form a cup body structural configuration covering the hip of wearer.

The present disclosure provides a new type of water spray head, which increases the flushing range of the excrement cleaning device and improves the effect of cleaning.

In one embodiment, the present disclosure provides an excrement cleaning device, comprising a body made of hard material and a cup body made of soft material. The body comprises a flushing member. The cup body is sleeved on the body. Wherein, the flushing member comprises a tube base, a hose, and a nozzle. The tube base is bent upward at an angle from the bottom of the main body. One end of the hose is connected to the tube base. The nozzle is connected to the other end of the hose. Wherein, the hardness of the tube base and the nozzle is greater than the hardness of the hose, which allows water pressure through the tube base to the hose to shake the nozzle for increasing cleaning range.

By arranging a hose between the nozzle and the rigid tube base having a bent configuration, a water pressure through the tube base to the hose would shake the nozzle for increasing the cleaning (spraying) range.

In one embodiment, the present disclosure provides a method for cleaning excrements with the excrement cleaning device. Through this method, the excrement cleaning device can be cleaned at the same time as the user is cleaned to achieve a truly automatic excrement cleaning device that is self-care-free for the user.

According to one embodiment of the present disclosure, a method for cleaning excrements with an excrement cleaning device first makes the excrement cleaning device to be in a negative pressure state, then two times of flushing and three times of cleaning are performed in order under the negative pressure state, followed by air-jetting the tubes and finally releasing the negative pressure state to dry the excrement cleaning device.

It should be understood, however, that this summary may not contain all aspects and embodiments of the present disclosure, that this summary is not meant to be limiting or restrictive in any manner, and that the disclosure as disclosed herein will be understood by one of ordinary skill in the art to encompass obvious improvements and modifications thereto.

BRIEF DESCRIPTION OF THE DRAWINGS

The features of the exemplary embodiments believed to be novel and the elements and/or the steps characteristic of the exemplary embodiments are set forth with particularity in the appended claims. The Figures are for illustration purposes only and are not drawn to scale. The exemplary embodiments, both as to organization and method of operation, may best be understood by reference to the detailed description which follows taken in conjunction with the accompanying drawings in which:

DETAILED DESCRIPTION OF THE EMBODIMENTS

The present disclosure will now be described more fully hereinafter with reference to the accompanying drawings, in which exemplary embodiments of the disclosure are shown. This present disclosure may, however, be embodied in many different forms and should not be construed as limited to the embodiments set forth herein. Rather, these embodiments are provided so that this present disclosure will be thorough and complete, and will fully convey the scope of the present disclosure to those skilled in the art.

Figure 1:
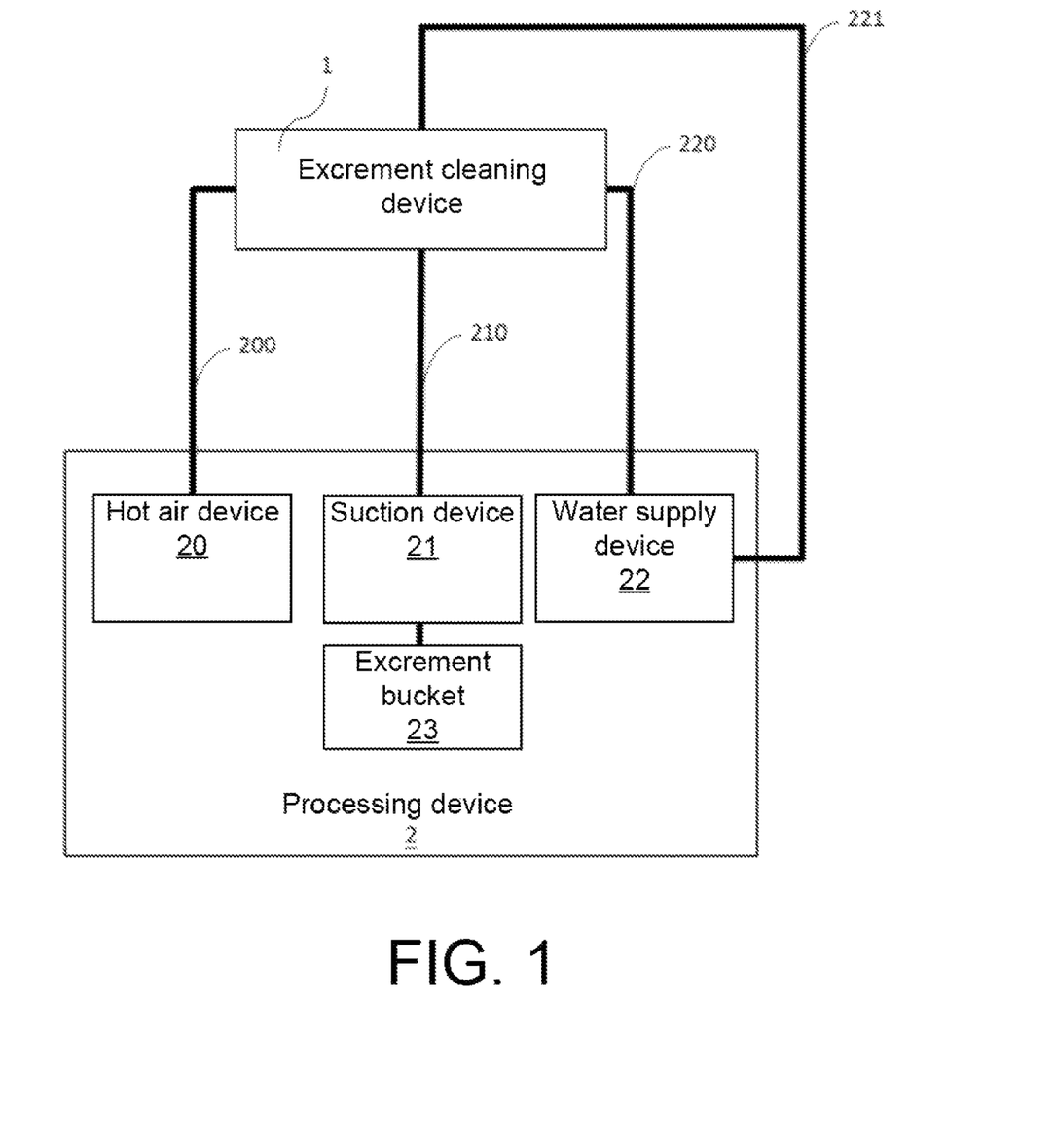
FIG. 1 is a schematic diagram of a system architecture applying an excrement cleaning device of the present disclosure.
Figure 2:
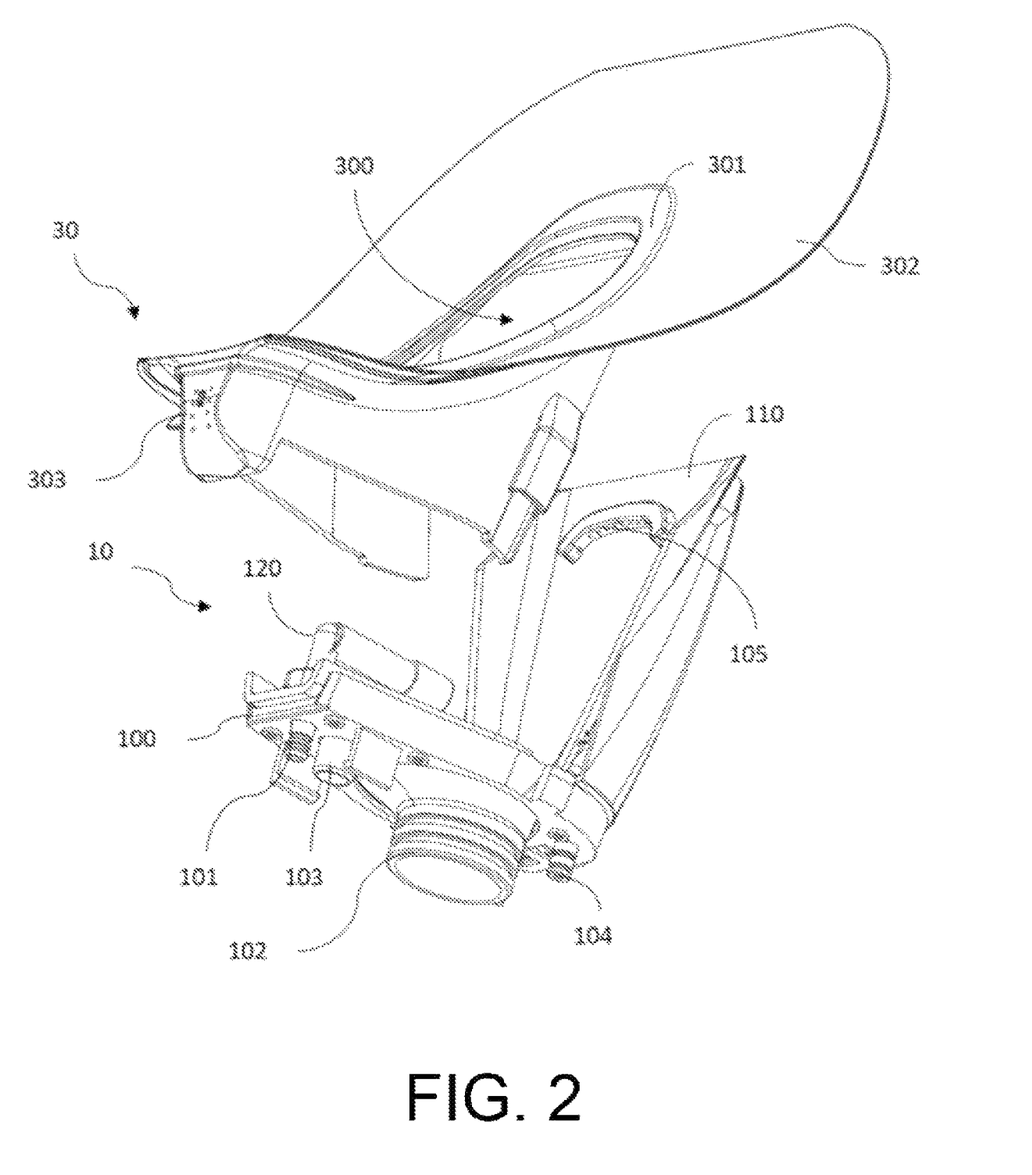
FIG. 2 is an exploded schematic diagram of the excrement cleaning device of an embodiment of the present disclosure.
Figure 3:
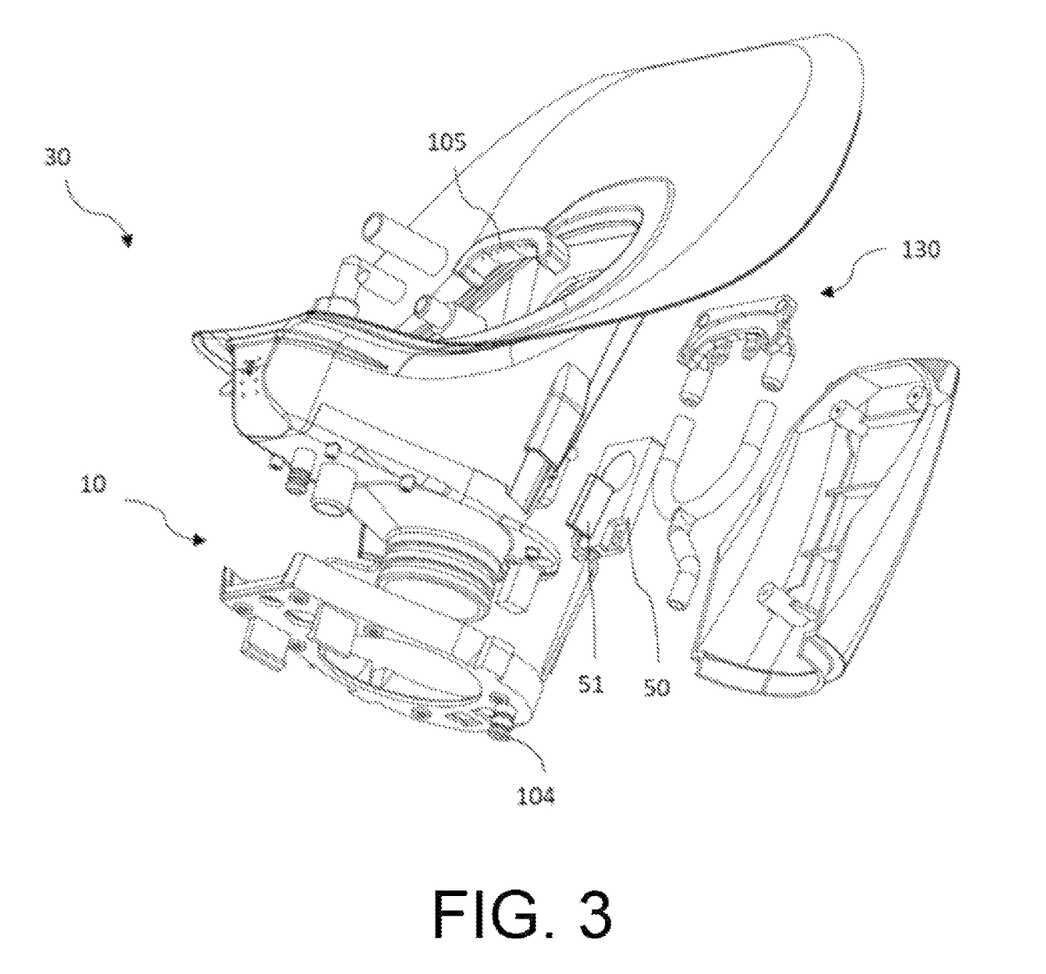
FIG. 3 is a schematic diagram from another perspective of FIG. 2.

FIG. 1 is a schematic diagram of a system architecture applying an excrement cleaning device of the present disclosure. FIG. 2 is an exploded schematic diagram of the excrement cleaning device of an embodiment of the present disclosure. FIG. 3 is a schematic diagram from another perspective of FIG. 2. In this embodiment, as shown in FIG. 1, an excrement cleaning device 1 connected to a processing device 2 is provided. The excrement cleaning device can be worn by user and is provided with a sensor to detect whether excrement is present. The processing device 2 comprises a suction device 21, a water supply device 22, and a hot air device 20, which are respectively connected to the excrement cleaning device 1 through tubes. The processing device is driven by the sensor (not shown) of the excrement cleaning device 1, and after the discharged excrement is collected into the excrement bucket 23 through the suction device 21, cleaning operations such as washing and drying are performed.

Referring to FIG. 2 and FIG. 3, according to one embodiment, an excrement cleaning device 1 comprises a body 10 made of hard material and a cup body 30 made of soft material. The body 10 comprises a base 100, a support base 110, a flushing member 120, and a cleaning member 130. The base 100 comprises a flushing port 101, a suction inlet 102, a hot air port 103, and a cleaning port 104. The flushing port 101 is connected to the processing device 2 (water supply device 22) through a flushing water tube 220. The suction inlet 102 is connected to the processing device 2 (suction device 21) through an excrement tube 210. The hot air port 103 is connected to the processing device 2 (hot air device 20) through a hot air tube 200. The cleaning port 104 is connected to the processing device 2 (water supply device 22) through a cleaning water tube 221. The support base 110 is longitudinally formed at a rear end of the base 100, and the top of the support base 110 comprises at least one water outlet 105. The flushing member 120 is extendingly disposed at the base 100 and is connected to the flushing port 101. The cleaning member 130 is embedded in the support base 110, one end of the cleaning member 130 is connected to the cleaning port 104, while the other end is connected to the water outlet 105. One side of the cup body 30 is disposed at the body 10 while the other side comprises a cup opening 300. A periphery of the cup opening 300 is provided with a lip 301 in contact with hip of user. A sheet body 302 of the lip 301 extends outward to form a hip enclosing area corresponding to the hip.

The excrement cleaning device 1 further comprises a weight sensor 50 and a pair of optical sensors 51 for sensing excrement. The weight sensor 50 is disposed in the support base 110, and the pair of optical sensors 51 are respectively disposed on two sidewalls of the cup body 30 below the lip 301.

The cup body 30 and the body 10 form a configuration with a curved hip enclosing area. The support base 110 can be used as the main fulcrum, and the sheet body 302 can increase the friction and dispersion pressure between the hip and the excrement cleaning device 1, so it would be more stable when wearing and practicing the excrement cleaning device 1 and there is no need to worry about the dislocation of the cup body 30 as the user turning over or moving. Besides, a front end of the cup body 30 can be extended to cover the male genitals, or other independent urine cleaning devices can be used in combination.

It should be noted that the material of the support base 110 is relatively hard compared to that of the cup body 30. The sheet body 302 is essentially a soft silicone sheet, the size of which can be changed according to the size of the wearer's hip, as wearing an appropriately sized product improves comfort. Besides, the cup body 30 is provided with at least one supplementary pressure air inlet 303 close to a front end of the base 100. When the suction device 21 starts the suction to collect the air with the excrement into the excrement bucket 23, the supplementary pressure air inlet 303 would introduce external air into the cup body 30. In this way, in addition to forming a negative pressure state inside the cup body 30, the inflow of external air would form a wind pressure to generate a forward airflow, which is beneficial for the suction device 21 to suck the excrement into the excrement bucket 23. Thus, there would be no issues of the leakage of odorous gas and the overflow of the excrement.

Since the support base 110 and the base 100 are arranged at a right angle of nearly 90 degrees, so when the user is in bed, the side view of the body 10 would be L-shaped, the support base 110 would be placed on the mattress stably, and the tube connected to the base 100 would be disposed at the inner thigh and the groin of the user. Thus, tubes connecting the excrement cleaning device and the processing device would no longer need to pass through the mattress, and the wearing comfort and the using flexibility would be greatly improved.

In actual practice, the entire excrement cleaning device is combined with a wearable trousers fabric (not shown) to facilitate wearing and fixing. The weight sensor 50 and the optical sensor 51 are respectively electrically connected to the processing device 2 for sensing excrement and driving the processing device 2. When excrement falls from the anus, it would be detected by the optical sensors 51 on two sides first, then the excrement would fall to an inner wall of the support base 110 and be detected by the weight sensor 50. The dual sensor design improves detection accuracy. Wire grooves are provided in the trouser fabric to hold or guide the electrical wires between the sensor and the processing device. Since the wiring techniques of electrical connection are known to those skilled in the art, it would not be described herein.

Figure 4:
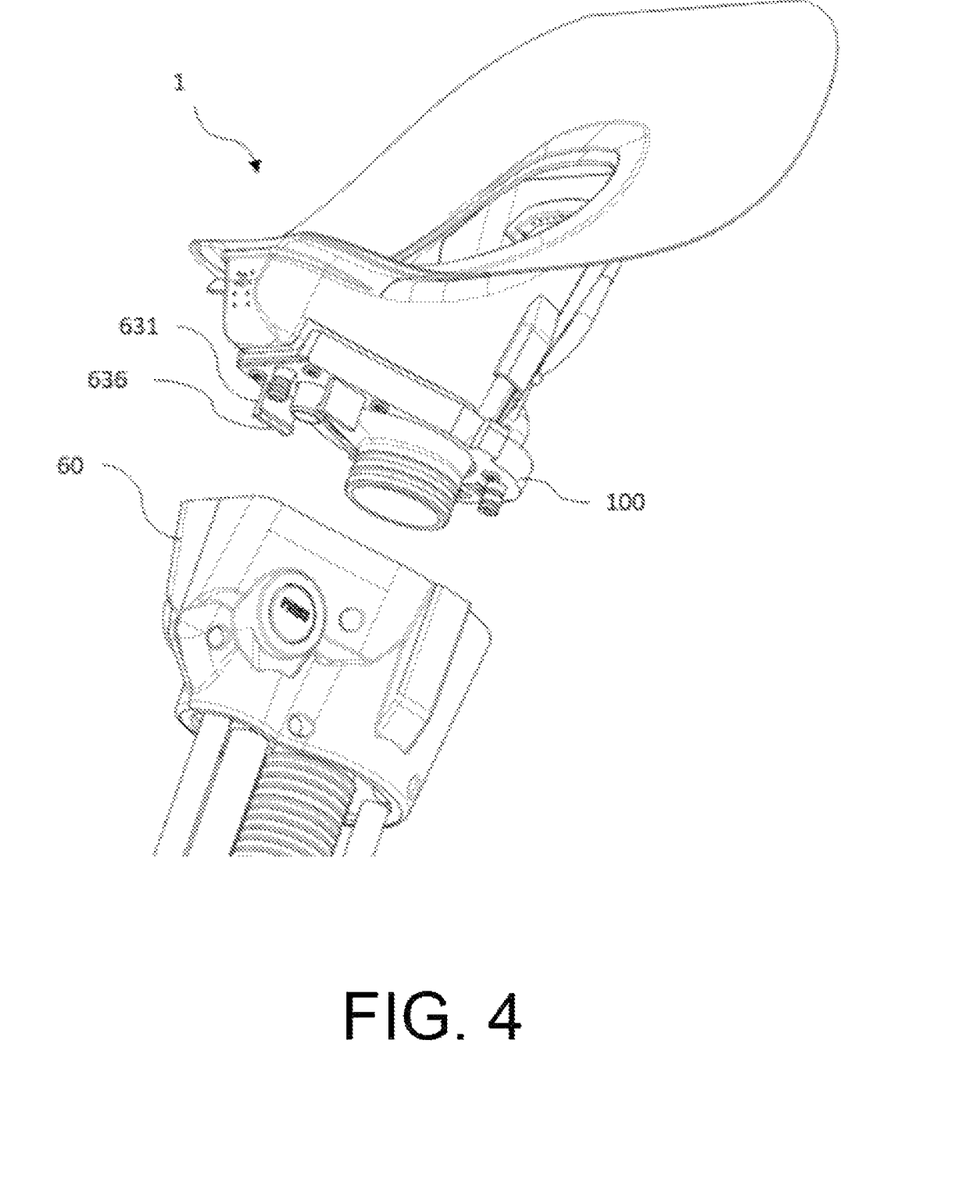
FIG. 4 is a schematic diagram of the excrement cleaning device of another embodiment of the present disclosure.
Figure 5:
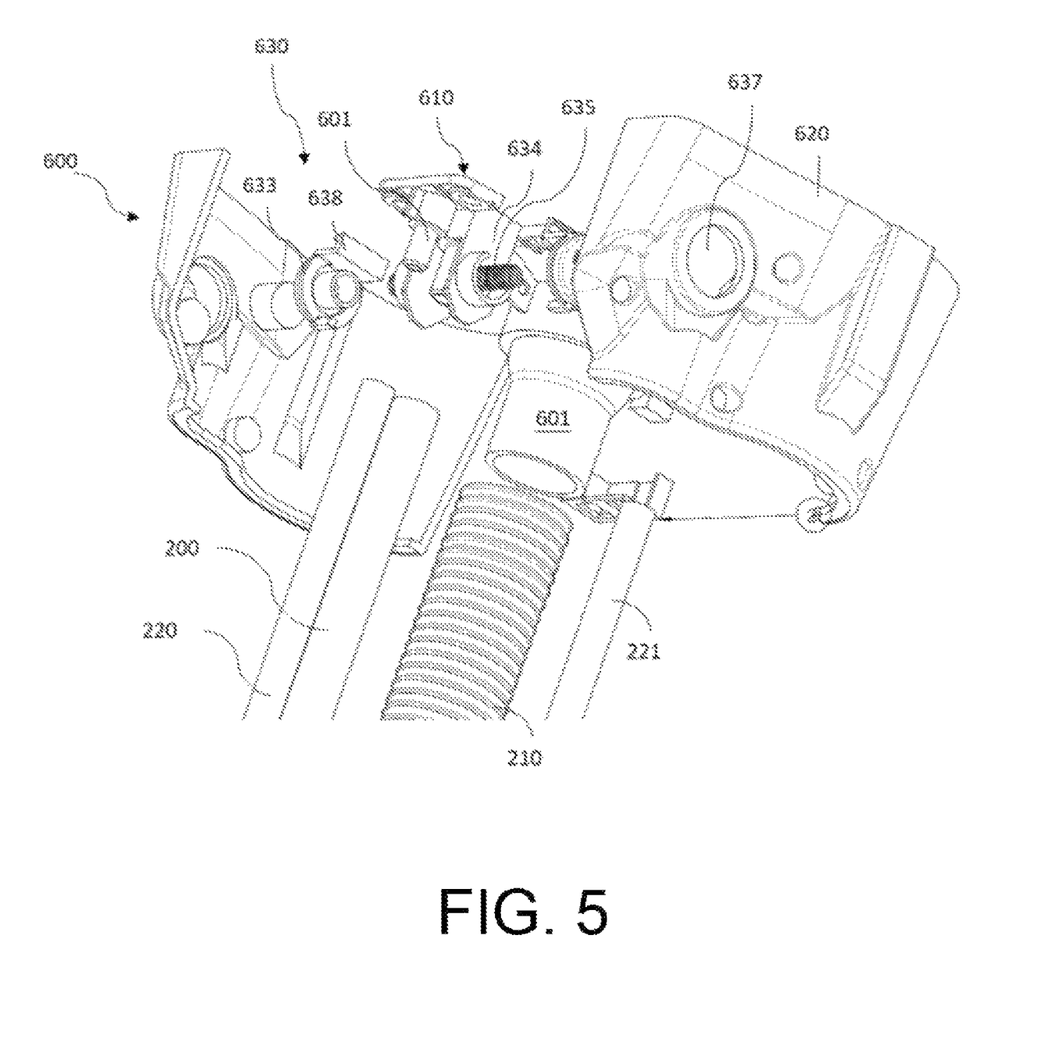
FIG. 5 is an exploded schematic diagram of a quick-release joint of FIG. 4.

FIG. 4 is a schematic diagram of the excrement cleaning device of another embodiment of the present disclosure. FIG. 5 is an exploded schematic diagram of a quick-release joint of FIG. 4. To improve the convenience of tube disassembly and assembly, the excrement cleaning device may further comprise a quick-release joint 60. Compared with the previous embodiment, when the cleaning device is to be disassembled, it is necessary to disassemble the communicating tubes piece by piece. With the quick-release joint 60, the tubes connected between the excrement cleaning device 1 and the processing device can be quickly disassembled and assembled.

In this embodiment, the quick-release joint 60 is fixedly connected to the flushing water tube 220, the excrement tube 210, the hot air tube 200, and the cleaning water tube 221, and is disposed at the bottom of the base 100 to form a buckle mechanism 600. The buckle mechanism 600 enables the quick-release joint 60 to be attached to and detached from the body 10.

The quick-release joint 60 comprises a plurality of communication ports 601. The diameter of the communication ports 601 respectively corresponds to the diameter of the connected flushing water tube 220, the excrement tube 210, the hot air tube 200, and the cleaning water tube 221.

As shown in FIG. 5, the buckle mechanism 600 comprises a connecting base 610, a housing 620, and a pair of detent components 630. The plurality of communication ports 601 pass through the connecting base 610. The pair of detent components 630 are disposed on two sides of the quick-release joint 60 and are covered by the housing 620.

Each of the detent components 630 comprises a first detent member 631, a second detent member 632, a button 633, a baffle 634, and a spring 635. One end of the first detent member 631 is disposed on the bottom surface of the base 100 and extends downward, and the other end comprises a first hook 636. The button 633 is disposed in the through hole 637 of the housing 620, and one side surface of the button 633 is exposed outside of the housing 620. The second detent member 632 is disposed in the housing 620, one end of the second detent member 632 is disposed at a position of the button 633 corresponding to the first detent member 631 and extends upwards, and the other end comprises a second hook 638 engaged with the first hook 636. The baffle 634 is disposed on the bottom surface of the connecting base 610 and extends downward. The spring 635 is disposed between the button 633 and the baffle 634, one end of the spring 635 abuts against the other side of the button 633 (inside the housing 620), and the other end abuts against the baffle 634. By applying an external force to the side surface of the button 633 exposed outside of the housing 620, the spring 635 can be pushed to pivot the second hook 638 to unhook the first hook 636.

To put it simply, when the connection between the excrement cleaning device and the processing device is to be dismantled, it is only necessary to press the button 633 to separate the base 100 from the quick-release joint 60.

Thus, compared with the conventional configuration which is quite complex, the present disclosure applies a simple two-piece modular configuration, so that the cup body having the cup opening and the sheet body are disposed on the body to form a cup-shaped configuration which covers the wearer. The quick-release joint 60 allows the tube connected between the excrement cleaning device 1 and the processing device to be quickly detached and assembled.

Figure 6A:
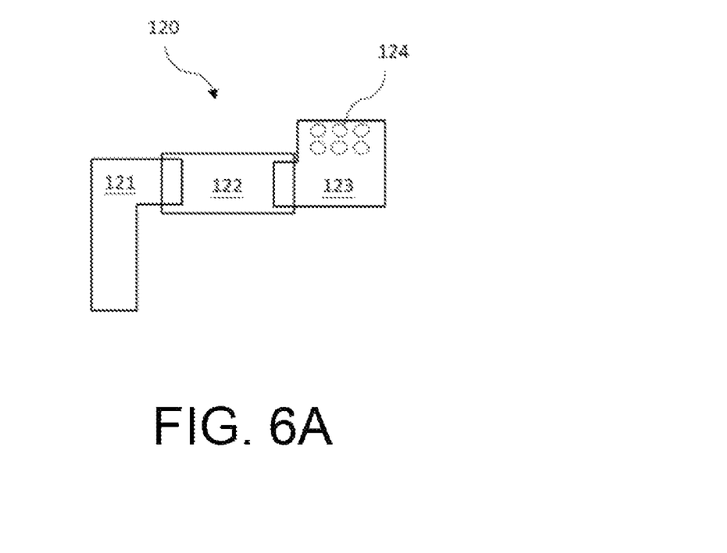
FIG. 6A is a schematic diagram of a flushing member of an embodiment of the present disclosure.
Figure 6B:
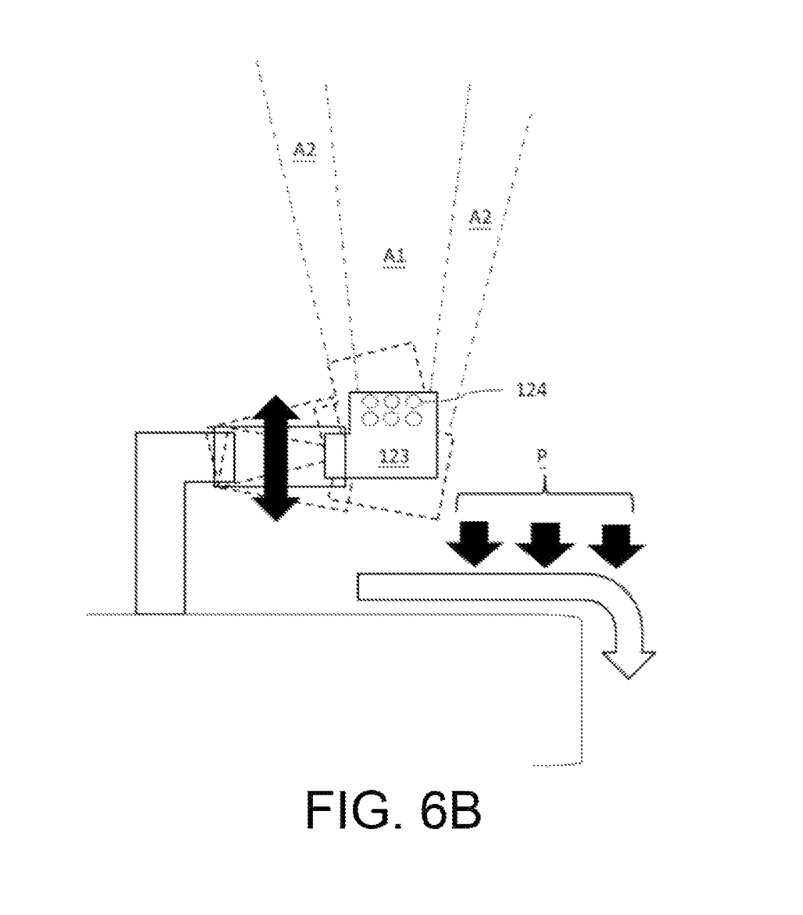
FIG. 6B is another schematic diagram of FIG. 6A.

FIG. 6A is a schematic diagram of a flushing member of an embodiment of the present disclosure. FIG. 6B is another schematic diagram of FIG. 6A. In this embodiment, the flushing member 120 comprises a tube base 121, a hose 122, and a nozzle 123. The tube base 121 is disposed at the bottom of the body, and is bent and extended at an angle after reaching a height. One end of the hose 122 is sleeved and connected to the tube base 121, and the nozzle 123 is connected to the other end of the hose 122. The hose 122 is made of flexible material, and the hardness of the tube base 121 and the nozzle 123 is much greater than the hardness of the hose 122. When the water supply device delivers water to the flushing member 120, a water pressure through the tube base 121 to the hose 122 would shake the nozzle 123 for increasing the cleaning range.

In one embodiment, a surface of the nozzle 133 is provided with a plurality of spray holes 124, which spray water toward the hip of user. In addition to the original water distribution area of the plurality of spray holes 124 as the first flushing area A1, the actual spraying range of the nozzle 123 would additionally cover a second flushing area A2 as the water pressure shakes the hose 122. Especially in the state of negative pressure suction, the inhaled air flow would allow the nozzle 123 to shake severely, the second flushing area A2 hence would be further expanded.

Besides, as shown in FIG. 6 with FIG. 2, the height of the nozzle 123 on a horizontal plane is higher than that of the supplementary pressure air inlet 303. So, when the suction device is activated, external air would be sucked by the suction device to form an airflow, and the flowing airflow would form an air pressure P. When the height of the spray holes 124 is higher than a surface of the wind pressure P, the spraying would not be affected, and the excrement would not contaminate the nozzle 123 during the flushing process with water. Even if it is contaminated, the nozzle 123 can be removed at any time for cleaning or replacement.

Figure 7:
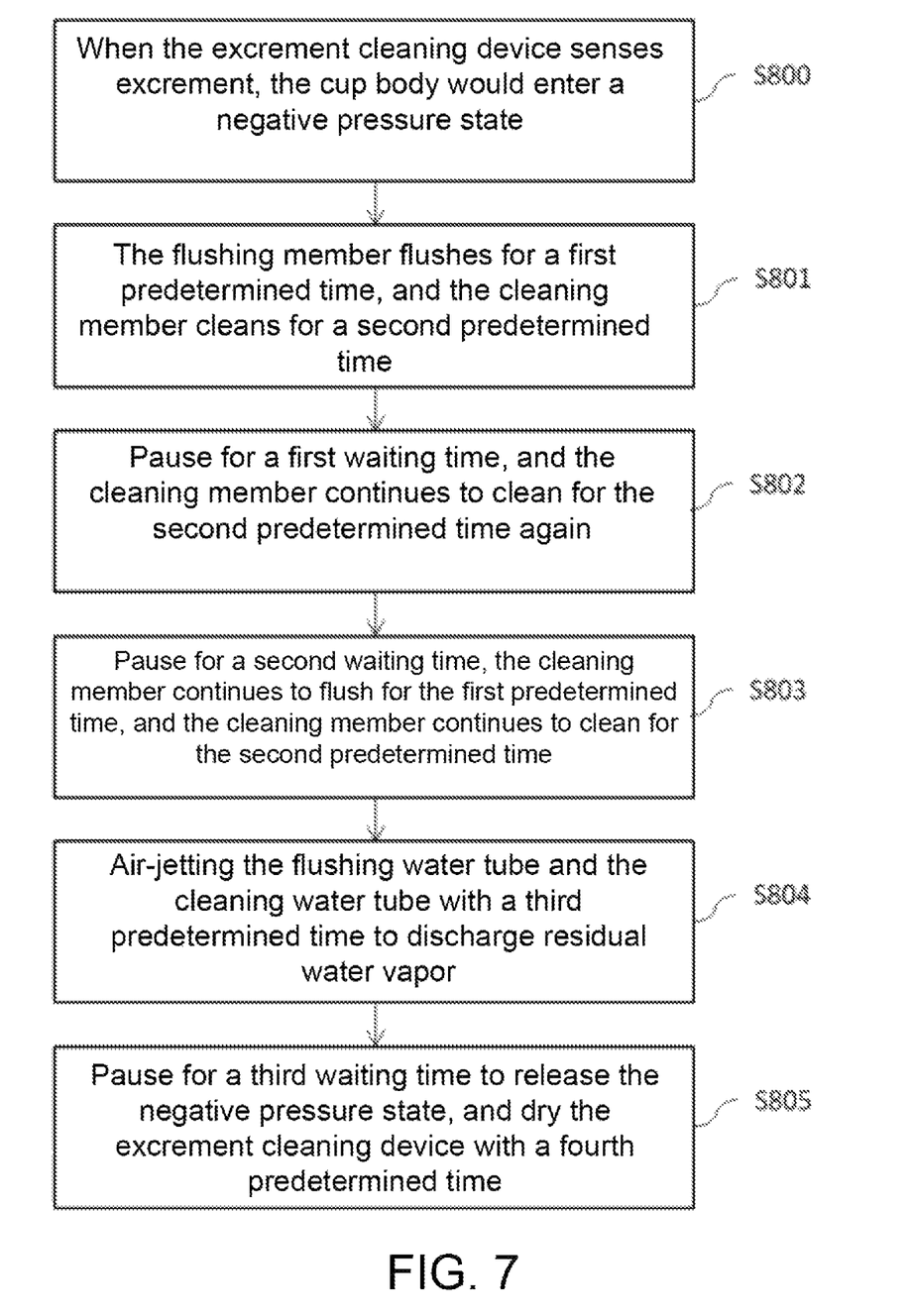
FIG. 7 is a flow chart of a method for cleaning excrements with the aforementioned excrement cleaning device of the present disclosure.

FIG. 7 is a flow chart of a method for cleaning excrements with the aforementioned excrement cleaning device of the present disclosure. For a better understanding of the present disclosure, the following descriptions are provided with flowcharts and processing steps. The method for cleaning excrements with the excrement cleaning device comprises the following steps in order:

S800: When the excrement cleaning device senses excrement, the cup body would enter a negative pressure state.

S801: The flushing member flushes for a first predetermined time, and the cleaning member cleans for a second predetermined time.

S802: Pause for a first waiting time, and the cleaning member continues to clean for the second predetermined time again.

S803: Pause for a second waiting time, the cleaning member continues to flush for the first predetermined time, and the cleaning member continues to clean for the second predetermined time.

S804: Air-jet the flushing water tube and the cleaning water tube with a third predetermined time to discharge residual water vapor.

S805: Pause for a third waiting time to release the negative pressure state, and dry the excrement cleaning device with a fourth predetermined time.

In one embodiment, the first predetermined time or the second predetermined time may be between 1 and 5 seconds, the first waiting time or the second waiting time may be between 160 and 180 seconds, the third predetermined time is between 50 and 70 seconds, the third waiting time is between 50 and 70 seconds, and the fourth predetermined time is between 230 and 250 seconds. The aforementioned time in seconds could be changed according to preferences or actual application requirements.

The flushing refers to the action of the flushing member spraying water on organs of user, and the cleaning refers to the water outlet cleaning wall surfaces of the excrement cleaning device. It is worth noting that the cleaning method of the present disclosure does not simply increase the cleaning effect through multiple flushing, but performs adaptive switching cleaning for the process of human excretion. In this way, the sticky excrement can be flushed reliably, and the subsequent cleaning operation for the excrement cleaning device can be completed.

The present disclosure provides a cleaning method for excrements with an excrement cleaning device, which firstly brings the excrement cleaning device into a negative pressure state, then perform two flushes and three washes in order followed by air-jetting the tubes under the negative pressure, and finally release the negative pressure state to dry the excrement cleaning device for excellent cleaning.

Although the present disclosure has been explained in relation to its preferred embodiment, it does not intend to limit the present disclosure. It will be apparent to those skilled in the art having regard to this present disclosure that other modifications of the exemplary embodiments beyond those embodiments specifically described here may be made without departing from the spirit of the disclosure. Accordingly, such modifications are considered within the scope of the disclosure as limited solely by the appended claims.

What is claimed is:

1. A device for cleaning excrement and configured to connect to a processing device comprising:
    a body made of hard material, comprising:
        a base comprising
            a flushing port connected to the processing device through a flushing water tube;
            a suction inlet connected to the processing device through an excrement tube;
            a hot air port connected to the processing device through a hot air tube; and
            a cleaning port connected to the processing device through a cleaning water tube;
        a support base longitudinally formed at a rear end of the base, at least one water outlet disposed at the top of the support base;
        a flushing member extendingly disposed at the base and connected to the flushing port; and
        a cleaning member embedded in the support base wherein one end of the cleaning member is connected to the cleaning port and the other end of the cleaning member is connected to the water outlet; and
    a cup body made of soft material, one side of which disposed at the body and the other side of the cup body configured with a cup opening, a periphery of the cup opening configured with a lip for contacting a hip of a user, a sheet body of the lip extending outward to form a hip enclosing area corresponding to the hip.

2. The device according to claim 1, further comprising:
    a weight sensor disposed in the support base; and
    a pair of optical sensors respectively disposed on two sidewalls of the cup body below the lip.

3. The device according to claim 2, further comprising a quick-release joint fixedly connected to the flushing water tube, the excrement tube, the hot air tube, and the cleaning water tube, wherein the quick-release joint is disposed at the bottom of the base to form a buckle mechanism for the quick-release joint to be selectively attached to or detached from the body.

4. The device according to claim 3, wherein the quick-release joint comprises a plurality of communication ports, wherein the diameter of each of the communication ports corresponds to the diameter of the connected flushing water tube, the excrement tube, the hot air tube, and the cleaning water tube.

5. The device according to claim 4, wherein the buckle mechanism comprises a pair of detent components disposed on two sides of the quick-release joint, wherein the buckle mechanism is covered by a housing, wherein the plurality of communication ports pass through a connecting base, wherein each detent component comprises:
    a first detent member, one end of the first detent member disposed on a bottom surface of the base and extends downward, and the other end of the first detent member having a first hook;
    a button disposed at a through hole of the housing for exposing the button outside the housing;
    a second detent member disposed in the housing, one end of the second detent member disposed at a position of the button corresponding to the first detent member and extends upward, and the other end of the second detent member having a second hook hooked with the first hook;
    a baffle extending downward from a bottom surface of the connecting base; and
    a spring, one end of the spring configured to abut against a side surface of the button and the other end of the spring configured to abut against the baffle, wherein the button pushes the spring by an external force for the second hook to disengage from the first hook.

6. The device according to claim 1, wherein a front end of the cup body close to the base comprises at least one supplementary pressure air inlet.

7. A device for cleaning excrement comprising a body made of hard material, and a cup body made of soft material, the body comprising a flushing member, and the cup body sleeved on the body, wherein the flushing member comprises:
    a tube base bent upward at an angle from the bottom of the main body;
    a hose, one end of the hose connected to the tube base; and
    a nozzle connected to the other end of the hose;
    wherein the hardness of the tube base and the nozzle are greater than the hardness of the hose, which allows water pressure through the tube base to the hose to shake the nozzle for increasing cleaning range.

8. A method for cleaning excrement with the device according to claim 1, comprising act of:
    enabling the cup body to be in a negative pressure state when the excrement cleaning device senses excrement;
    allowing the flushing member to continue to flush for a first predetermined time and the cleaning member to clean for a second predetermined time;
    pausing for a first waiting time, and allowing the cleaning member continue to clean for the second predetermined time;
    pausing for a second waiting time, and allowing the cleaning member continue to flush for the first predetermined time and allowing the cleaning member continue to clean for the second predetermined time;

air-jetting the flushing water tube and the cleaning water tube for a third predetermined time to discharge the residual water vapor; and pausing for a third waiting time, releasing the negative pressure state and drying the excrement cleaning device for a fourth predetermined time.

\* \* \* \* \*